United States Patent [19]

Pinder

[11] Patent Number: 5,217,038
[45] Date of Patent: Jun. 8, 1993

[54] APPARATUS FOR EMPTYING A HAZARDOUS WASTE CONTAINER

[75] Inventor: Stanley N. Pinder, Brandon, Fla.

[73] Assignee: PPPK, Inc., Brooklyn, N.Y.

[21] Appl. No.: 860,877

[22] Filed: Mar. 31, 1992

[51] Int. Cl.⁵ .............................................. F04F 5/02
[52] U.S. Cl. .................... 137/216; 137/562; 417/181
[58] Field of Search ............. 417/181; 137/562, 216; 604/319, 321

[56] References Cited

U.S. PATENT DOCUMENTS

| | | | |
|---|---|---|---|
| 905,818 | 12/1908 | Langford | 417/181 |
| 3,183,923 | 5/1965 | Henrikson | 137/216 |
| 4,014,052 | 3/1977 | Wolos | 137/562 |
| 4,422,829 | 12/1983 | Buchanan | 417/181 X |
| 5,083,587 | 1/1992 | Tarjan | 137/562 X |

*Primary Examiner*—Robert G. Nilson
*Attorney, Agent, or Firm*—Joseph C. Mason, Jr.; Ronald E. Smith

[57] ABSTRACT

Pleural and other body fluids that may harbor disease organisms are emptied from a container by connecting the container to a venturi device and running water under pressure through the venturi device so that the fluids in the container are entrained into the flow of water under pressure. The outlet of the venturi device is in fluid communication with a sanitary sewer.

1 Claim, 2 Drawing Sheets

APPARATUS FOR EMPTYING A HAZARDOUS WASTE CONTAINER

TECHNICAL FIELD

This invention relates to devices having utility in the field of hazardous waste disposal. More particularly, it relates to a device having utility in emptying a container having blood and other body fluids therein.

BACKGROUND ART

Blood and other body fluids are lost when a patient undergoes surgery, and many different containers have been invented for collecting said lost blood and other fluids. Some of the containers are designed to be disposed of while still containing the fluids therein, and other containers are designed to be emptied so that they can be reused. Other containers are designed to be emptied but not reused. Typically, a flexible hose extends from the patient's body to the collection device and the fluids are continually vacuumed into the collection device throughout the surgical procedure.

One of the most widely used fluid collection devices is a chest-drainage device known as the Pleur-Vac; it is made by Deknatel (a Pfizer company) and is the subject of U.S. Pat. Nos. 4,018,224, 4,955,874, and others. The leading end of a first flexible hose extends from the patient's chest cavity to an inlet of the Pleur-Vac, and a second flexible hose or suction tube extends from an outlet of the unit to a source of negative Pressure; the unit is designed so that blood and pleural fluid collect in the device and cannot enter the suction tube. The device is also designed so that the fluids entering it are trapped in a labyrinth, and cannot be easily emptied therefrom without exposing the operator and others in the operating theater to the hazards of contact by splashing and aerosolization.

When the surgical procedure is completed, the Pleur-Vac is disconnected from the patient and the fluids collected therein may be safely and legally disposed of by introducing them into a sanitary sewer. However, the only known means of emptying the unit is to manually and alternately rotate it so that the fluids may escape the labyrinth and flow therefrom under the influence of gravity. Thus the person charged with this task, and others, are exposed to contact.

OSHA regulations require that blood, pleural fluids, and other body fluids be handled in such a manner that the handlers and those in the vicinity of the handlers are not exposed to such fluids or aerosols thereof, and recommend that the fluids be carefully introduced to the sanitary sewer at or near the point of generation. The only known and present method of emptying the units probably violates those regulations. Therefore, the device has been traditionally disposed of without attempting to empty the bio-hazardous body fluids contained therein.

Disposal of the Pleur-Vac, or other drainage collection units of the same general type, while fluids are still held therewithin is not recommended for several reasons. On-site, as well as off-site transportation of the Pleuro-Vac requires many handlings. Every handling of the unit during the transportation process to its final point of disposal greatly increases the risk, to handlers and the public, of exposure to its contents. Further, medical waste incinerators are not designed to process liquids.

Thus, the present inventor has identified a need for a device capable of safely emptying containers having hazardous fluids therein, but the prior art when considered as a whole in accordance with the requirements of law at the time the present invention was made neither taught nor suggested to those of ordinary skill in the pertinent art how such a device could be provided.

DISCLOSURE OF INVENTION

The present invention provides an eductor apparatus having two inlets, a venturi device, an outlet and appropriate control means. The first inlet is in fluid communication with a source of hot water under pressure and the second inlet receives the leading end of a flexible tube from a container filled with fluids. The outlet is in fluid communication with a waste discharge tube that terminates in a sanitary sewer connection.

The novel unit is permanently installed at a basin of the type commonly found in operating rooms. A permanent hose or pipe is installed between the hot water supply of the existing basin and the unit's first inlet, and an appropriate valve is positioned in said hose or pipe. The container to be emptied is placed into the basin and is supported by the bottom wall thereof throughout the emptying procedure. The container or trailing end of the flexible tube that extended from the patient to the container remains attached to the container, but the patient or leading end thereof is attached to the second inlet of the novel device. The valve is then opened and hot water is introduced into the novel eductor; it flows through the venturi device and into the sanitary sewer through the waste discharge pipe. A venturi effect created by the flow of said hot water entrains the fluids out of the container and into the stream of hot water so that said fluids are carried by said stream to said sanitary sewer. Some microorganisms are killed by the hot water, and those that survive are greatly diluted. The treatment facility associated with the sanitary sewer destroys the surviving organisms.

Thus it is seen that the primary object of this invention is to provide a device that ensures the safety of hospital personnel who are required to empty containers filled with fluids that might be contaminated with viral agents or other health-threatening organisms.

A more specific object is to accomplish the foregoing object with a simple, inexpensive and easy to operate device.

Another important object is to provide a device having utility in emptying containers of many differing types, not just those dedicated to the containment of hazardous fluids.

These and other objects, features and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

Similar reference numerals refer to similar parts throughout the several views of the drawings.

BEST MODES FOR CARRYING OUT THE INVENTION

Figure 1:
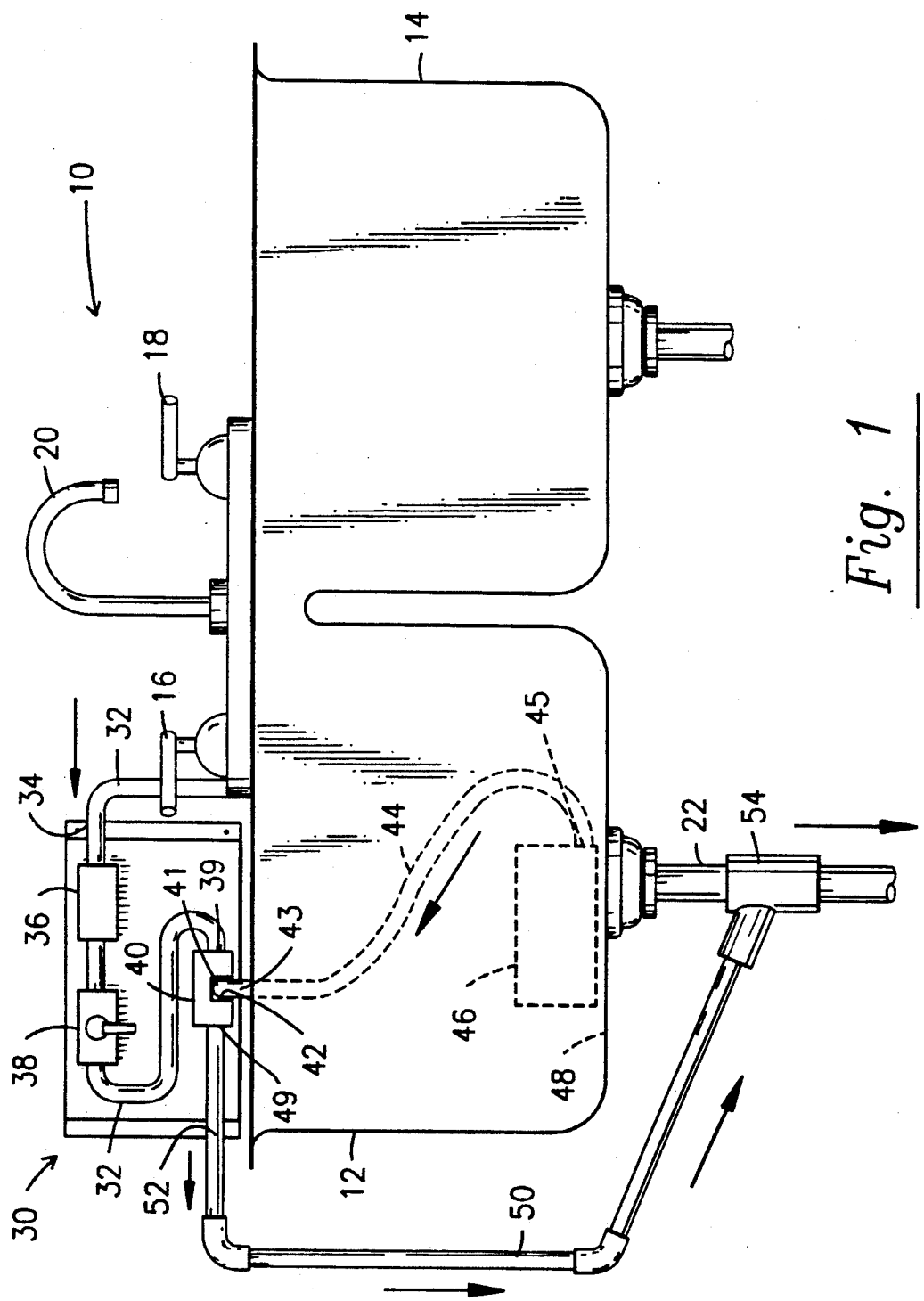
FIG. 1 is a side elevational view of a first embodiment of the novel device and its environment.

Referring now to FIG. 1, it will there be seen that an illustrative embodiment of the invention is shown in a typical environment that is denoted as a whole by the reference numeral 10.

Environment 10 preferably includes a dual basin sink having chambers 12 and 14, hot and cold water taps 16 and 18, faucet 20, and a drain pipe 22 that is connected to a sanitary sewer.

The novel unit is denoted 30 as a whole; it may be provided in the form of a hollow housing the cover of which is removed in FIG. 1 to reveal the interior thereof. Unit 30 is mounted to a wall above the sink and adjacent hot water tap 16. A first conduit in the form of hot water-carrying pipe 32 enters unit 30 at first inlet 34, which is adapted to receive said pipe, and is connected to a vacuum breaker 36 that is positioned within the device 30. Vacuum breaker 36 precludes reverse travel of water, i.e., it ensures that water will flow in a forward direction from a source of water under pressure, through hot water pipe 32, and to the vacuum breaker 36, i.e., not in an opposite direction relative to said forward flow.

Pipe 32 then continues to an on-off ball valve 38 which performs the function its name expresses; other suitable valve means may be employed as well. Thus, tap 16 may be left open at all times so that the flow of hot water through pipe 32 is controlled by valve 38. Pipe 32 then extends from the outlet of valve 38 to a first inlet 39 of a venturi device 40 of the coaxial type. Venturi device 40 also includes a second inlet 41 to which is connected the leading end 43 of a second conduit in the form of flexible tube 44 having a trailing end 45 connected to the container 46 to be emptied. Note that container 46 is supported by bottom wall 48 of chamber 12. Although not shown in FIG. 1, a check valve is positioned in fluid communication with second conduit 44 so that fluids in said container 46 may flow only in a forward direction from said container toward said venturi device and not in a reverse flow relative to said forward flow.

An elongate third conduit in the form of waste discharge pipe 50 is connected in fluid communication between the outlet 49 of the venturi device 40 and the sanitary sewer 22; note that tube 50 exits the housing for the novel device 30 at outlet 52 and connects with the sanitary sewer 22 at coupling 54. Coupling 54 is downstream of the conventional trap.

Although hot water is the preferred liquid fluid for operating the novel device, due to its ready availability and suitability, the use of different liquid fluids is within the scope of this invention.

To empty fluids from container 46, the leading end 43 of tube 44 is removed from the patient; the trailing end 45 thereof remains attached to container 46 as shown. Container 46 is then taken from the operating table area to the basin area which is typically just a few steps away. The leading end 43 of tube 44 is then affixed to the second inlet 42 of unit 30, and valve 38 is opened. Although not shown in FIG. 1, second inlet 42 is in fluid communication with second inlet 41 of venturi device 40. Thus, hot water flows sequentially through pipe 32, through venturi device 40, and to the sanitary sewer 22 through discharge pipe 50, and that flow of hot water entrains fluids from container 46 and carries them to said sanitary sewer as well. Container 46 can then be disposed of routinely. The hot water will kill a large number of viruses, bacteria, or other harmful organisms and those not killed will be greatly diluted before entering the sanitary sewer. When container 46 is empty (the Pleur-Vac and similar units are transparent), valve 38 is shut off and the leading end 43 of tube 44 is detached from inlet 42 of unit 30 so that said unit can be disposed of as aforesaid.

Figure 2:
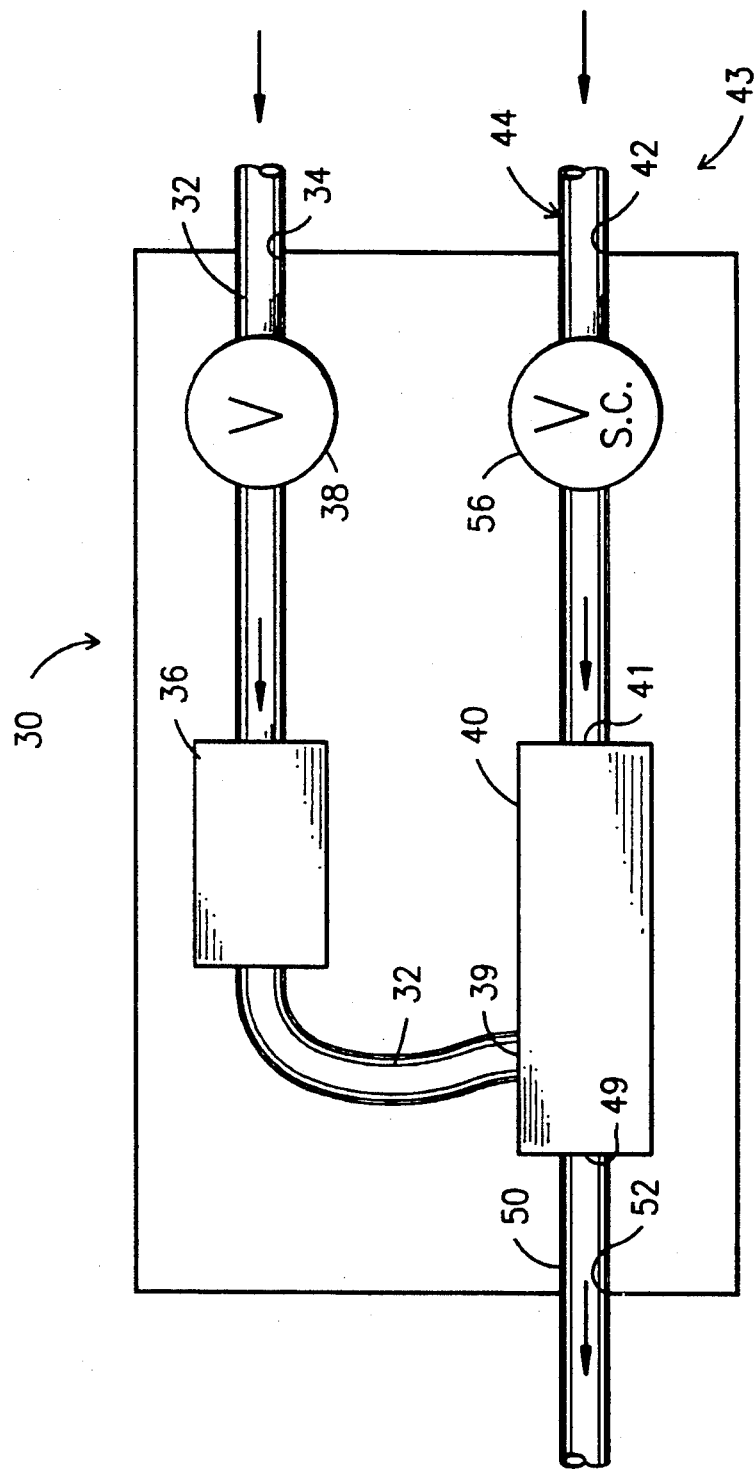
FIG. 2 is a side elevational view of a second embodiment thereof.

A slightly different embodiment of the inventive unit 30 is depicted in FIG. 2. The only difference in the embodiments of FIGS. 1 and 2 is the arrangement of the parts. i.e., the same parts are employed but are positioned differently. The above-mentioned check valve that allows fluids in container 46 to flow into unit 30 but which prevents reverse flow is provided in the form of a swing check valve and is denoted 56. Ball valve 38 is positioned upstream of vacuum breaker 36 in this embodiment, and the path of travel of pipe 32 between said valve 36 and the venturi device 40 is shortened in this second embodiment. Moreover, flexible tube 44 enters unit 30 at an end thereof instead of mid-length thereof as depicted in FIG. 1; said inlet is denoted 42 as in FIG. 1. The operation of both embodiments is the same. Both embodiments have two inlets and a single outlet; the inlets are the hot water or first inlet 34 and the suction or second inlet 42 where the leading end 43 of hose 44 is connected to device 30, and the outlet 52 is downstream of the venturi device 40 in both embodiments.

This invention is clearly new and useful. Moreover, it was not obvious to those of ordinary skill in this art at the time it was made, in view of the prior art considered as a whole as required by law.

It will thus be seen that the objects set forth above, and those made apparent from the foregoing description, are efficiently attained and since certain changes may be made in the above construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. An apparatus that removes fluids from a container, said apparatus being in fluid communication with a source of a preselected liquid fluid under pressure, comprising:

a first conduit in fluid communication with said source of a preselected liquid fluid under pressure;

a first on-off valve for selectively admitting said preselected liquid fluid into said first conduit;

said first on-off valve having a normally "open" configuration so that said preselected liquid fluid is always in said first conduit;

a second on-off valve, disposed in said first conduit downstream of said first on-off valve, for selectively admitting said preselected liquid fluid into the apparatus;

said second on-off valve having a normally "closed" configuration;

a venturi device through which flows said preselected liquid fluid only when said second on-off valve is placed in an "open" configuration by a human operator;

said second on-off valve being disposed between said first on-off valve and said venturi device;

a check valve disposed between said container and said venturi device so that fluids may flow in a forward direction from said container into said venturi device but not in a reverse direction relative to said forward direction;

a vacuum breaker disposed between said first on-off valve and sad venturi device so that said preselected liquid fluid under pressure flows in a forward direction from said firsts on-off valve to said venturi device but not in a reverse direction relative to said forward direction;

a second conduit for providing fluid communication between the interior of the container to be emptied and said venturi device; and a third conduit disposed in fluid communication between an outlet of said venturi device and a sanitary sewer;

whereby said preselected liquid fluid flowing through said venturi device entrains the fluids from said container and carries said fluids through said third conduit to said sanitary sewer only when said second on-off valve is opened by a human operator.

* * * * *